United States Patent [19]

Rosenthal et al.

[11] Patent Number: 5,162,361
[45] Date of Patent: Nov. 10, 1992

[54] METHOD OF TREATING DISEASES ASSOCIATED WITH ELEVATED LEVELS OF INTERLEUKIN 1

[75] Inventors: Gary J. Rosenthal, Chapel Hill; Yasuhida Kouchi; Emanuela Corsini, both of Durham; Benny Blaylock, Morrisville; Christine Comment, Carrboro; Michael Luster, New Hill; William Craig, Raleigh; Michael Taylor, Durham, all of N.C.

[73] Assignee: The United States of America as represented by the Secretary, Department of Health and Human Services, Washington, D.C.

[21] Appl. No.: 506,613

[22] Filed: Apr. 10, 1990

[51] Int. Cl.⁵ ........................................ A61K 31/415
[52] U.S. Cl. .................... 514/396; 514/397; 514/398; 514/399; 514/400; 514/401; 514/825; 514/838; 514/851; 514/885; 514/893; 514/921; 514/924
[58] Field of Search ............... 514/396, 397, 398, 399, 514/400, 401, 825, 863, 885, 886; 424/45

[56] References Cited

U.S. PATENT DOCUMENTS

| | | | |
|---|---|---|---|
| 4,073,922 | 2/1978 | Wyburn-Mason | 514/825 |
| 4,119,723 | 10/1978 | Wyburn-Mason | 514/398 |
| 4,183,941 | 1/1980 | Wyburn-Mason | 424/248.4 |
| 4,218,449 | 8/1980 | Wyburn-Mason | 424/248.4 |
| 4,376,124 | 3/1983 | Carlson et al. | 514/532 |
| 4,399,151 | 8/1983 | Sjoerdsma et al. | 424/319 |
| 4,426,384 | 1/1984 | Wyburn-Mason | 424/253 |
| 4,757,049 | 7/1988 | Plotnikoff | 514/17 |
| 4,804,651 | 2/1989 | Duvic et al. | 514/50 |
| 4,895,719 | 1/1990 | Radhakrishnan et al. | 424/45 |
| 4,906,476 | 3/1990 | Radhakrishnan | 424/450 |
| 4,920,016 | 4/1990 | Allen et al. | 424/450 |
| 4,933,347 | 6/1990 | Tidwell et al. | 514/636 |
| 4,956,355 | 9/1990 | Prendergast | 514/178 |
| 4,971,802 | 11/1990 | Tarcsay et al. | 514/885 |
| 4,983,397 | 1/1991 | Schroit et al. | 424/450 |
| 5,006,343 | 4/1991 | Benson et al. | 424/450 |
| 5,013,556 | 5/1991 | Woodle et al. | 424/450 |
| 5,026,687 | 6/1991 | Yarchoan et al. | 514/637 |

FOREIGN PATENT DOCUMENTS 2644471 2/1978 Fed. Rep. of Germany.

OTHER PUBLICATIONS

Ferrante et al. C.A. 103: 327g (1985).
Maloff et al., C.A. 111: 224962p (1989); C.A. 111: 192836g (1989).
Allison et al., C.A. 109: 228038y (1988); Connolly et al., C.A. 109: 67102x (1988).
De Young et al., C.A. 107: 168454c (1987); Abul et al., C.A. 106: 169298w (1987).
Domer et al., C.A. 108: 202733a (1988); Nair et al., C.A. 101: 17677c (1984); Dreher et al., C.A. 101: 103773n (1984).
Logan et al., C.A. 107: 198753s (1987); Buxade, C.A. 108: 132166s (1988); Scudeletti et al., C.A. 113: 52657r (1990).
Kusnecov et al., C.A. 112: 229863n (1990); Roth et al., C.A. 110: 133402u (1989); Ruso et al., C.A. 98: 209711a (1983).
Tarayre et al., C.A. 93: 639k (1980).
Rosenthal, G. J. et al., "Inhibition of Cytokine Secre- (List continued on next page.)

Primary Examiner—Shep K. Rose
Attorney, Agent, or Firm—Cushman, Darby & Cushman

[57] ABSTRACT

The present invention relates to a method of treating diseases associated with elevated levels of interleukin 1 (IL-1) including inflammatory diseases such as arthritis, skin hypersensitivity and endotoxemia. More specifically, the invention relates to a method for the treatment of such diseases in warm-blooded animals, such as humans, which comprises the administration of a therapeutically effective amount of an aromatic diamidine, sufficient to inhibit IL-1 release from IL-1 producing cells. The aromatic diamidine can also be used to block interleukin 6 (IL-6) and tumor necrosis factor from cells producing these cytokines.

28 Claims, 7 Drawing Sheets tion by Diamidine Compounds", FASEB J., vol. 4, Issue 7, Apr. 26, 1990, p. A1858, Abstracts of Joint Meeting, American Society of Biochemistry and Molecular Biology and American Association of Immunologists, New Orleans, Jun. 4-7, 1990—Oral Presentation, no full written article ever existed.

Rosenthal, G. J. et al., "Pentamidine: An Inhibitor of Interleukin-1 that Acts via a Post-Translational Event", Toxicology and Applied Pharmacology, vol. 107, issue 3, 1991, pp. 55-61.

Therapie 22(4) (Fr) 1967.

Debs et al., Successful Treatment with Aerosolized Pentamidine of Pneumocystis carinii Pneumonia in Rats, Antimicrobial Agents and Chemotherapy, vol. 31, No. 1, pp. 37-41, Jan. 1987.

Special Report, Aerosolized Pentamidine, The Latest on the Current Controversy, AIDS Patient Care, Apr. 1989.

Kasahara et al., The Role of Monokines in Granuloma Formation in Mice: The Ability of Interleukin 1 and Tumor Necrosis Factor-$\alpha$ to Induce Lung Granulomas, Clinical Immunology and Immunopathology 51, 419-425 (1989).

Girard et al., Pentamidine Aerosol in Prophylaxis and Treatment of Murine Pneumocystis carinii Pneumonia, Antimicrobial Agents and Chemotherapy, vol. 31, No. 7, pp. 978-981, Jul. 1987.

Shen et al., Pentamidine-Induced Pancreatic Beta-Cell Dysfunction, The American Journal of Medicine, vol. 86, pp. 726-728, Jun. 1989.

Ahmed et al., Effect of Anticancer Drugs on Cytokine Release, Int. J. Immunotherapy IV(3) 137-143 (1988).

| VEHICLE | PIT $10^{-5}$M | DEXAMETHASONE $10^{-6}$M |
|---|---|---|
| − + | − + | + |

IL-1α

α-TUBULIN

LANE A    LANE B

FIG. 2

METHOD OF TREATING DISEASES ASSOCIATED WITH ELEVATED LEVELS OF INTERLEUKIN 1

BACKGROUND OF THE INVENTION

1. Field of the Invention

The present invention relates to a method for inhibiting the release of interleukin 1 (IL-1) from IL-1 producing cells. More specifically, the invention relates to the treatment of diseases associated with elevated levels of IL-1.

2. Background Information

IL-1, a polypeptide cytokine with multiple biological properties, is a key mediator in immunological reactions as well as in the body's response to microbial invasion, inflammation and tissue injury. Since IL-1 is also highly inflammatory, down-regulation of its production has been an area of intense investigation. Specific pathological conditions where Il-1 diminution is beneficial include inflammatory diseases such as arthritis (where IL-1 is found in high concentrations in synovial fluid), endotoxemia (where, in conjunction with tumor necrosis factor the high concentration of IL-1 contributes to fever, hypothermia and hemodynamic shock), granulomatous diseases, fibrosis and hypersensitivity diseases (C. D. Dinarello, Review of Infect. Dis. 6, 51 (1986)).

At present, the most effective therapeutic agents to treat diseases associated with elevated IL-1 levels are corticosteroids. These act by inhibiting IL-1 transcription, although they may stimulate IL-1 translation of preformed IL-1 messenger RNA (mRNA). (P. J. Knudsen et al, J. Immunol. 139, 4129 (1987)). More recently, IL-1 receptor antagonists have been described that block the activity of IL-1 by binding to IL-1 receptors (C. H. Hannum et al., Nature 343, 336 (1990)).

It has now been found that aromatic diamidines are effective in treating diseases associated with elevated IL-1 levels. For example, 1,5-bis(4-amidinophenoxy)-pentane (pentamidine), an aromatic diamidine known for its effectiveness against AIDS related *Pneumocystis carinii* pneumonia, is a specific and effective inhibitor of cellular IL-1 release from macrophages. This may be associated with its putative ability to inhibit protease activity, since release of IL-1 from the membrane bound form is dependent upon the action of proteases which hydrolyze the peptide bond between the membrane anchoring sequence and the secreted form (K. Matsushima et al., J. Immunol. 136, 2883 (1986)).

The use of pentamidine as a blocker of IL-1 is an improvement over the use of corticosteroids. Pentamidine allows the protein to be translated, but blocks IL-1 at the level of release while corticosteroids block IL-1 at the level of mRNA. By contrast, corticosteroids block the message of IL-1 from being formed. This mechanism of action by corticosteroids is nonspecific, in that this class of drugs blocks the transcription of many biologically important proteins, as well as blocking IL-1 formation.

In addition, the mechanism by which pentamidine appears to act (the alteration of a postranslational protein modification event) allows it to be much more selective when compared to a representative corticosteroid, for example, dexamethasone. Such selectivity by pentamidine serves to spare other components of the immune system and circumvent the overt broad immunotoxicity that often results in decreased host resistance in patients undergoing corticosteroid therapy. This mechanism is a vast improvement over the immunodepressive activity of the corticosteroids.

1,5-di(4-imidazolinophenoxy)pentane, an aromatic substituted diamidine known for its effectiveness against *Trypanosoma rhodesiense* and *Plasmodium berghei* (E. Steck et al., Exp. Parasitol. 42, 404 (1981)), has also been found to be a specific and effective inhibitor of cellular IL-1 release from macrophages. This imidazoline is an analog to pentamidine and has a similar structure, with the exception that the terminal amidino groups are substituted with imidazoline moieties. Thus, this compound is believed to exert its effects in a way that is mechanistically similar to pentamidine.

SUMMARY OF THE INVENTION

The present invention relates to a method of treating diseases which are wholly or partly mediated by excess production of IL-1. More specifically, the present invention relates to a method of treating diseases associated with elevated levels of IL-1, comprising administering to warm blooded animals, including humans, in need of such treatment, a therapeutically effective amount of an aromatic diamidine.

In one embodiment, the invention relates to a method of treating diseases associated with elevated levels of IL-1, comprising administering to warm-blooded animals, including humans, in need of such treatment, a therapeutically effective amount of 1,5-bis(4-amidinophenoxy)pentane (pentamidine), which can be in the form of pentamidine isethionate.

In another embodiment, the invention relates to a method of treating diseases associated with elevated levels of IL-1, comprising administering to warm-blooded animals, including humans, in need of such treatment, a therapeutically effective amount of an imidazoline, which can be in the form of 1,5-di(4-imidazolinophenoxy)pentane.

Aromatic diamidines can also be used to inhibit the release of interleukin 6 (IL-6) and tumor necrosis factor from cells producing these cytokines.

It is a general object of the present invention to provide a method of treating a subject suffering from a disease associated with elevated levels of IL-1, while avoiding the adverse side effects and lack of specificity associated with art-recognized corticosteroid therapy.

Further objects and advantages of the invention will be clear to one skilled in the art from a reading of the description that follows.

(b) Western blot analysis of secreted protein.

FIG. 2. Northern blot analysis of IL-1α mRNA expression.

Figure 3:
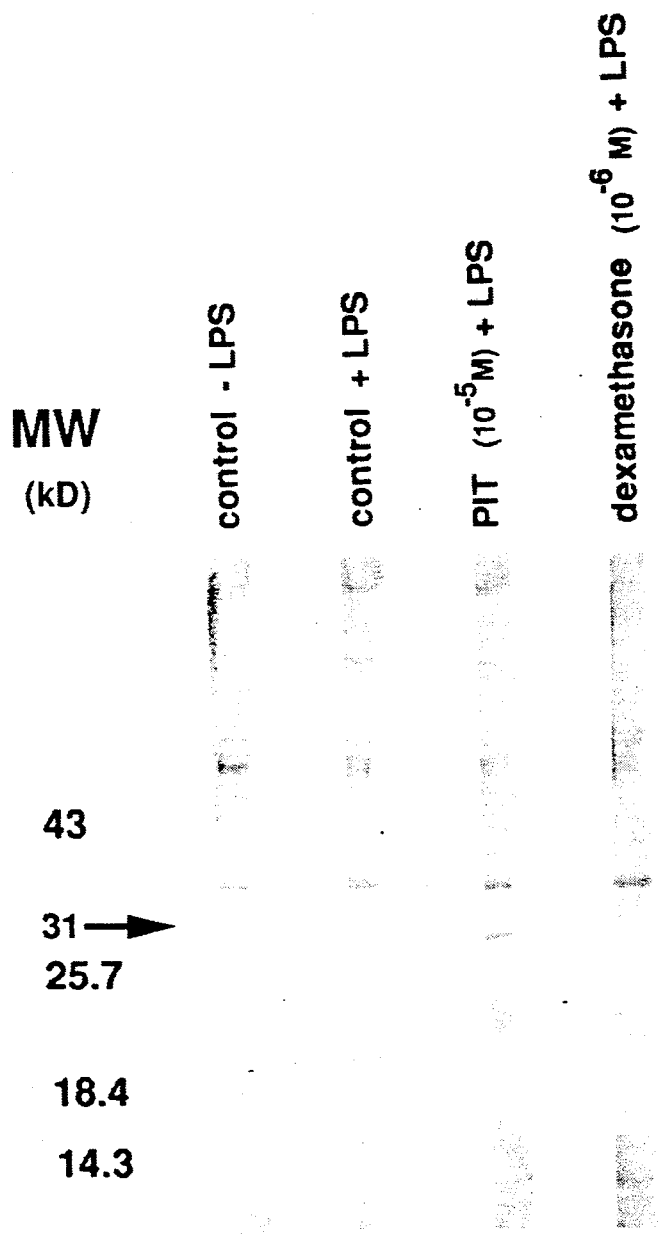

FIG. 3. Western blot analysis of cell associated IL-1α.

Figure 4:
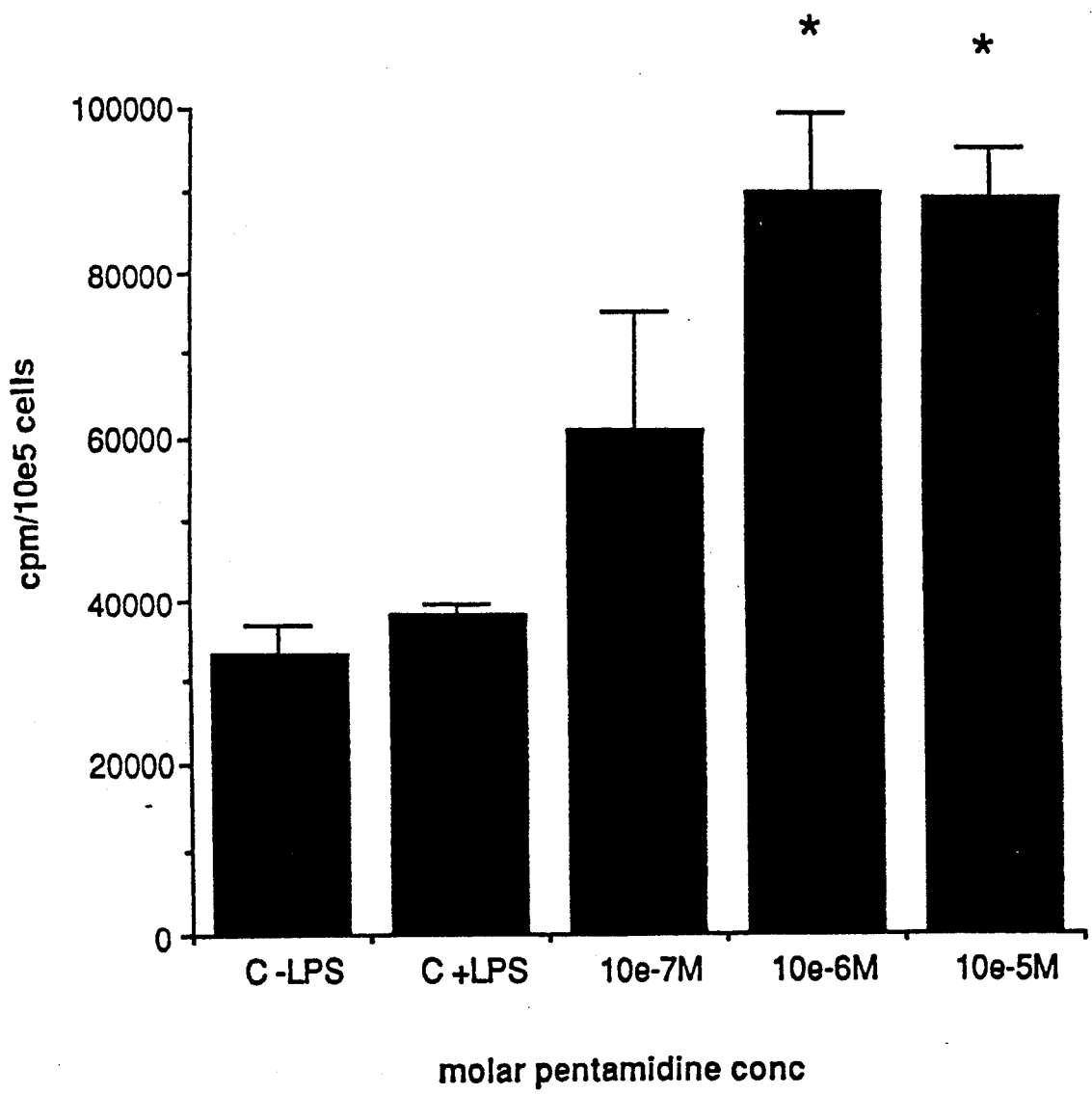

FIG. 4. Effect of pentamidine on membrane IL-1.

Figure 5:
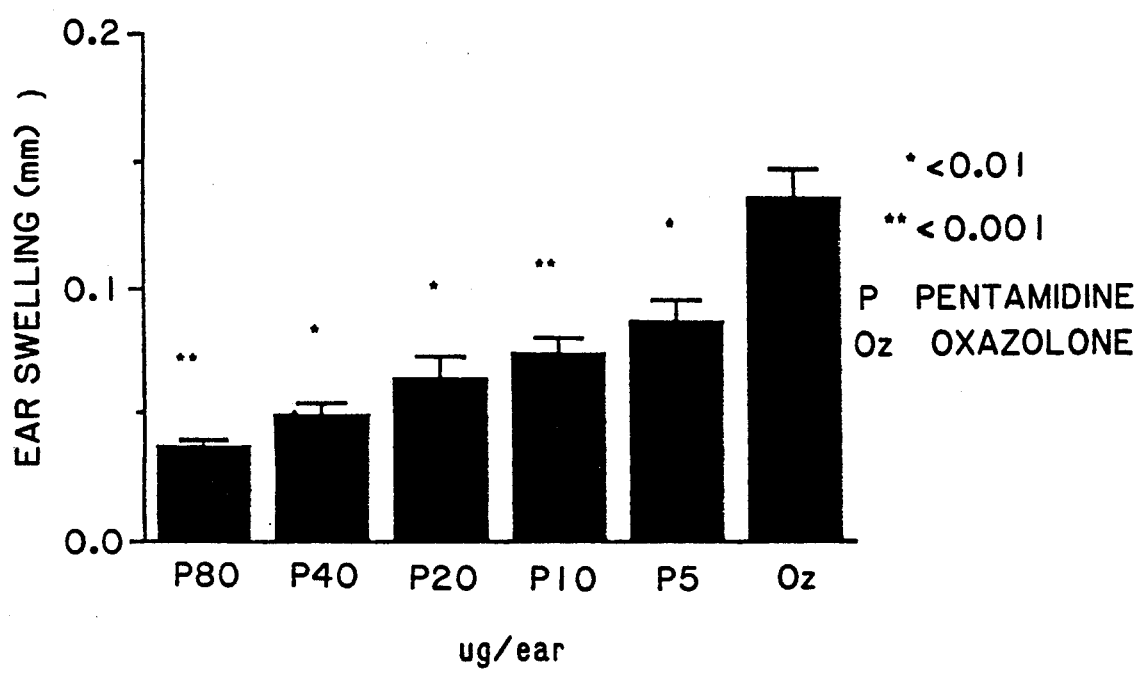

FIG. 5. Effect of pentamidine isethionate on oxazolone induced hypersensitivity assay.

Group 1—80 μg/ear pentamidine
Group 2—40 μg/ear pentamidine
Group 3—20 μg/ear pentamidine
Group 4—10 μg/ear pentamidine
Group 6—no treatment (oxazolone positive control).

FIG. 6. Pulmonary alveolar macrophage viability following 24 hour exposure to pentamidine.

Figure 7:
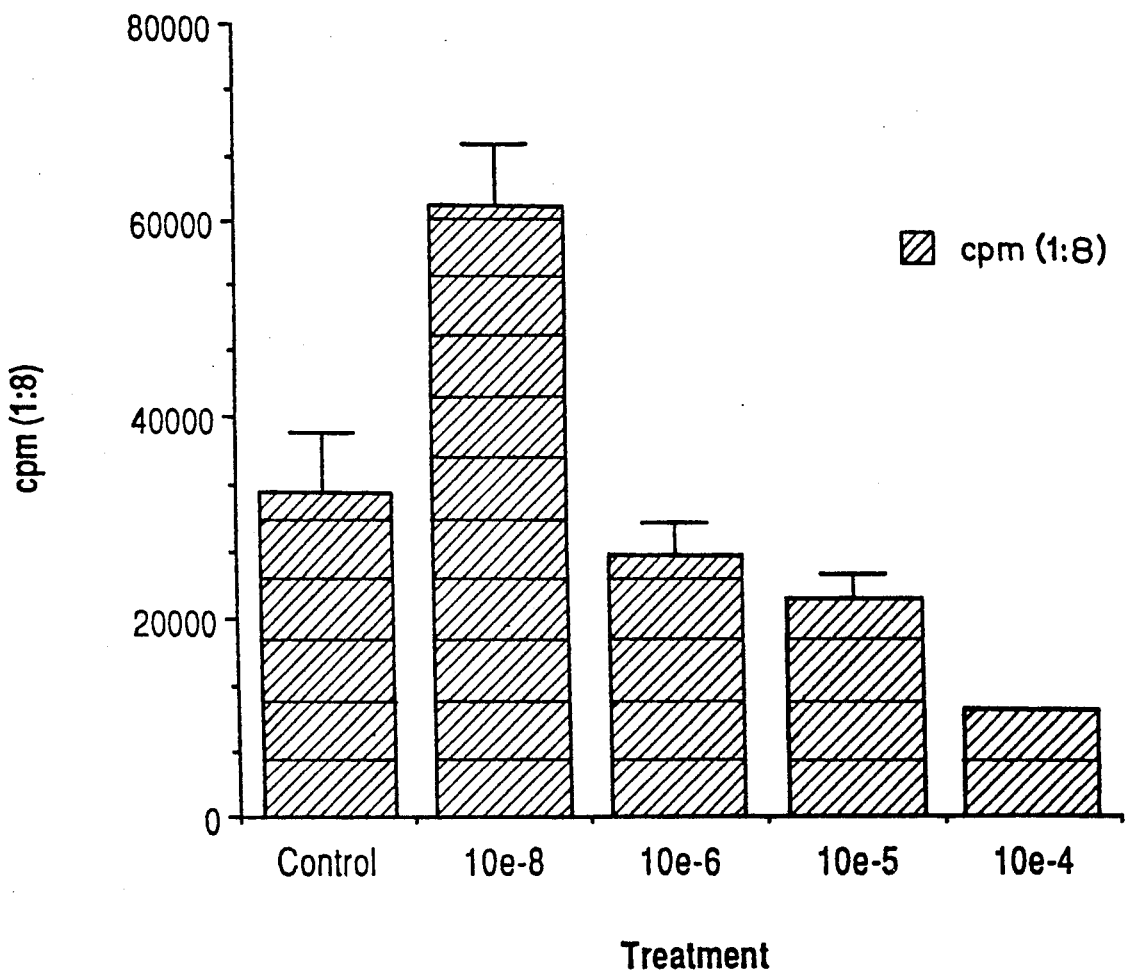

FIG. 7. Effect of an imidazoline on IL-1 production.

DETAILED DESCRIPTION OF THE INVENTION

The present invention is directed to a method of treating diseases associated with elevated levels of IL-1, comprising administering to warm-blooded animals, including humans, in need of such treatment, a therapeutically effective amount of an aromatic diamidine.

In one embodiment, the present invention is directed to a method of treating diseases associated with elevated levels of IL-1 comprising administering to warm-blooded animals, including humans, in need of such treatment, a therapeutically effective amount of 1,5-bis(4-amidinophenoxy)pentane (pentamidine). The pentamidine is advantageously in the form of pentamidine isethionate.

In another embodiment, the present invention is directed to a method of treating diseases associated with elevated levels of IL-1, comprising administering to warm-blooded animals, including humans, in need of such treatment, a therapeutically effective amount of an imidazoline derivative of pentamidine, specifically, 1,5-di(4-imidazolinophenoxy) pentane.

The diseases in which a diminution of IL-1 is beneficial include, but are not limited to, inflammatory diseases, such as arthritis, skin hypersensitivity, glomerulonephritis, septicemia including endotoxemia, pulmonary granulomas, pulmonary fibrosis, cirrhosis, sarcoidosis, tuberculosis, chronic granulomatous disease, dysfunctional clot formation, transplant rejection, and all diseases and conditions, including fever, associated with the release of acute phase reactants by hepatocytes.

The pharmaceutical formulations of the present invention comprise, as an active ingredient, an aromatic diamidine, for example, pentamidine or its imidazoline substituted derivative, together with a pharmaceutically acceptable carrier. The active ingredient is present in the composition in an amount sufficient to wholly or partially block IL-1 release from IL-1 producing cells. One skilled in the art would be able to determine when it would be desirable to wholly block IL-1 release and when it would be desirable to partially block IL-1 release. The composition of the invention can be formulated so as to be suitable, for example, for oral, nasal, parenteral, topical, transdermal or rectal administration.

Administration of the pharmaceutical formulation may, for example, be in the form of aerosols, ointments, creams, gels, tablets, capsules, pills, coated tablets, suppositories, powder, dusting powder or in liquid form.

The individual dosages are, for example:

(a) up to 650 mg per dose, and advantageously about 300 mg per dose, in the case of medicinal forms for inhalation (aerosols or solutions), (b) 15 mg active ingredient/kg animal in the case of parenteral medicinal forms (for example, intravenous or intramuscular), and (c) up to 1% active ingredient in solution in the case of medicinal forms for dermal application. Appropriate individual dosage sizes can be readily determined by one skilled in the art.

The aromatic diamidines can also be used to inhibit the release of IL-6 and tumor necrosis factor from cells producing these cytokines.

The frequency of administration and the amount of active ingredient to be administered to effect treatment of a particular disease associated with elevated levels of IL-1 can readily be determined by one skilled in the art.

Pentamidine, the best known of the aromatic diamidine compounds currently used as protazoacidal agents, is used in the treatment of AIDS related *Pneumocystis carinii* pneumonia. The therapeutic use of pentamidine in the treatment of AIDS has recently utilized the pulmonary route of exposure via aerosol administration. Because the alveolar macrophage is among the first of the immune cells to come into contact with pentamidine, the pentamidine induced modulation of the immune functions of this cell were investigated.

As discussed in detail below, Northern blot analysis demonstrates pentamidine's lack of effect on mRNA expression compared to the corticosteroid, dexamethasone. Western blot analysis of intracellular IL-1 demonstrates that pentamidine allows proper translation of the protein, while Western blot analysis of secreted IL-1 demonstrates the nearly complete block in the release of the intracellular IL-1.

Dose response studies were performed to determine the molar concentration at which pentamidine reduced viability in normal rat macrophages. No significant loss in cell viability is seen at concentrations $\leq 10^{-5}M$. In normal human macrophages, pentamidine blocks IL-1 secretion at a concentration of $10^{-5}M$ (see Example 5). This blockage was shown using an enzyme linked immunosorbant assay with specific antibody to IL-1$\beta$.

It has also been observed that pentamidine ($10^{-5}M$) blocks the secretion of tumor necrosis factor in rat macrophages (42 units/ml - pentamidine vs. 82 units/ml - control), as well as tumor necrosis factor and IL-6 in human macrophages, where at a concentration of $10^{-5}M$ pentamidine, tumor necrosis factor and IL-6 secretion are suppressed > 50%. These additional cytokines are also very influential mediators in inflammatory diseases. These data are the only known studies showing pentamidine's blockage of IL-6 and tumor necrosis factor.

An imidazoline has also been shown to have the ability to block IL-1 and tumor necrosis factor in rat macrophages, and is less toxic to the cell with an in vitro $LD_{50} > 10^{-4}$.

Figure 1:
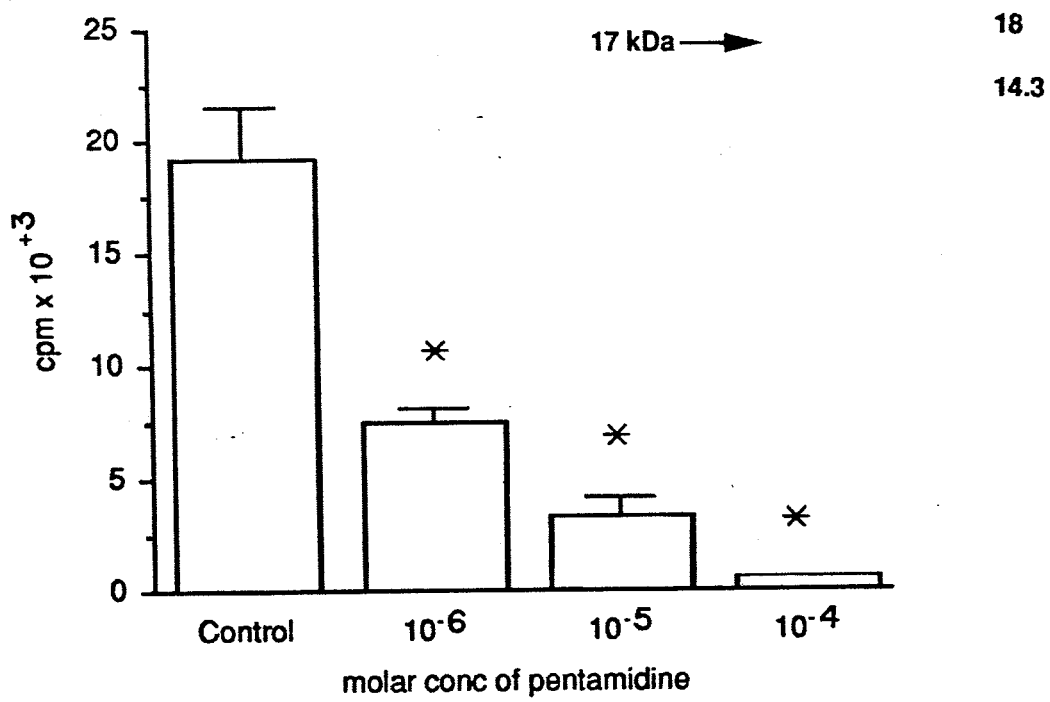
FIG. 1. (a) IL-1 release from pentamidine exposed rat pulmonary alveolar macrophages.

Interleukin 1 release from pentamidine exposed rat pulmonary alveolar macrophages decreased in a concentration dependant manner in supernatant fluid 24 hours post-exposure to the stimulus lipolysaccharide (FIG. 1a). This observation was confirmed by Western blot analysis of secreted protein (FIG. 1b) which demonstrated the lack of a lipopolysaccharide inducible IL-1 band reacting with antibody to murine IL-1$\alpha$. Since the classical inhibitors of IL-1, corticosteroids, have been shown to act at the level of gene transcription (P. J. Knudsen et al, J. Immunol. 139, 4129 (1987)), the present inventors sought to determine whether pentamidine induces its suppressive activity in a similar manner. Specific transcription of IL-1$\alpha$ mRNA synthesis was assessed by incubating cells with and without 10 $\mu$M pentamidine or 1 $\mu$M of the corticosteroid, dexamethasone in the presence or absence of lipopolysaccharide (LPS). At the end of a 3 hour incubation period, the cells were lysed and the total cellular RNA was collected, blotted onto a nitrocellulose filter and probed with $^{32}P$-labeled IL-1$\alpha$ cDNA. FIG. 2 shows that both untreated cells and pentamidine treated cells expressed similar amounts of IL-1$\alpha$ mRNA, indicating that blockage of cytokine secretion is not at the level of transcription. In contrast, mRNA for IL-1$\alpha$ was not seen in dexamethasone treated cells.

To determine the effect of pentamidine on cellular stores of IL-1, intracellular levels of IL-1 were quantitated by incubating cells with and without 10 μM pentamidine and LPS for 24 hours. At the end of this incubation period, the cells were washed, lysed and the total cellular protein was collected for Western blot analysis. FIG. 3 shows a representative Western blot of such studies. In both control and pentamidine treated cells, antiserum to murine IL-1α bound to a protein that migrated to approximately 31 kD in the presence of LPS. This is in agreement with the generally accepted existence of a precursor form of IL-1 with a molecular weight in the range of 31–33 kD (J. Giri et al., J. Immunol. 134, 343 (1985)). In contrast to pentamidine, cells treated with dexamethasone did not express the precursor from of IL-1α (FIG. 3).

Kurt-Jones et al. (Proc. Natl., Acad. Sci. USA 82, 1204 (1985)) first demonstrated IL-1 activity on the plasma membrane (mIL-1) of peritoneal macrophages, and subsequent studies have similarly identified a membrane bound protein of approximately 31 kD with the biological and chemical characteristics of IL-1 (D. Brody et al., J. Immunol. 143, 1183 (1989)). It has been postulated that since the immune response requires cell-to-cell interaction, mIL-1 may be a relevant form in the activation of lymphocytes (M. Hurme et al., Scand. J. Immunol. 27 (1988)). The observation of substantial levels of cell associated IL-1 with both Western blot analysis (FIG. 3) and bioassay raised the question of whether this biologically active precursor IL-1 was localizing and perhaps accumulating on the membrane of pentamidine treated macrophages. As shown in FIG. 4, the amount of bioactive mIL-1 was increased in a dose related manner in pentamidine exposed cells, a finding that correlates inversely with the suppression of the secreted form.

In contrast to pentamidine, the immunodepressrve activity of corticosteroids has been known for many years (T. R. Cupps et al., Immunological. Rev 65, 133 (1982); A. S. Fauci, J. Immunopharmacol. 1, 1 (1979)). Unfortunately, the pleotropic nature of steroids, influencing all components of the immune system, have often rendered their use tenuous considering the lowered resistance of steroid treated hosts to a variety of infectious agents. To assess other immunomodulatory effects of pentamidine in comparison to dexamethasone, two other measures of macrophage function were examined; phagocytosis and Ia antigen expression. As seen in Example 5, in Table 1, pentamidine did not modulate the phagocytic capacity of alveolar macrophages nor did it influence the mean concentration of Ia molecules on Ia positive cells. In contrast, dexamethasone clearly demonstrated its broad immunosuppressive action on these two macrophage functions.

These data taken together indicate that the mechanism of pentamidine induced inhibition of IL-1 occurs via alteration in the post-translational modification of the protein. Specifically, the cellular target plays a role in the intracellular and/or membrane cleavage of the 31 kDa pro-IL-1 to a 17 kDa secreted form. As yet, the mechanisms underlying IL-1 release are only partially understood, although the precursor form appears to undergo enzymatic cleavage prior to release from the cell (C. Gunther et al., Immunobiol. 178, 436, (1989); Y. Kobayashi et al., J. Immunol. 140, 2279 (1988)). The intracellular proteases suggested to be responsible for this processing include cathepsins (C. Gunther et al., Immunobiol. 178, 436 (1989)), tissue plasminogen activator and plasmin (K. Matsushima et al., J. Immunol. 136, 2883 (1986)), and trypsin (K. Matsushima et al., J. Immunol. 136, 2883 (1986); 0. Bakocuhe et al., J. Immunol. 138, 4249 (1987)). Pentamidine is a well known protease inhibitor (S. Vonderfecht et al., J. Clin. Invest. 82, 2011 (1988); Y. Klemes et al., Differentiation 27, 141 (1984)) and it is possible that its action on IL-1 release is mediated by this anti-protease activity. Regardless, the diminished IL-1 secretion induced by pentamidine offers a mechanistically unique and relatively specific inhibitor of IL-1.

At least two members of IL-1 ($\alpha$ and $\beta$) have been identified (reviewed in J. J. Oppenheim et al., Immunol. Today, 7, 45 (1986)), and are the translation products of two distinct genes, each gene coding for a precursor of approximately 31kDa to 33kDa (J. Giri et al., J. Immunol. 134, 343 (1985)) which are subsequently processed to the secreted form (17kDa). In the murine system, IL-1α appears to be the biologically active membrane bound form as well as the predominant form of released IL-1, and for these reasons, this form of IL-1 was focused on in the studies that led to this invention. As such, it is not necessarily possible to extrapolate such data to IL-1β. However, in humans, IL-1β is the predominant form of the secreted cytokine, and along these lines, decreased IL-1β release by human macrophages at similar concentrations as those reported herein have been observed (Example 5) indicating that the mechanism of action of pentamidine in IL-1 inhibition is not species specific and is not limited to the α form of the cytokine.

IL-1 proteins are involved in a wide range of immunologic and inflammatory responses and also have endocrine function, which are attributed to their ability to modulate proliferation, maturation and functional activity of a broad spectrum of cell types (C. D. Dinarello, Review of Infect. Dis. 6, 51 (1986)). Pharmacologic inhibition of cytokines, particularly IL-1, are expected to have a wide variety of therapeutic applications in inflammatory diseases including arthritis, granulomas of various organs, and fibrosis. Current therapeutics used for this purpose are the corticosteroids which, while effective inhibitors of IL-1, also affect macrophage functions as well as other immunological and nonimmunological responses. This lack of specificity often limit their therapeutic value. In contrast to the relative lack of immunologic specificity of corticosteroids, the immunologic specificity of pentamidine in inhibiting the secretion of IL-1 is demonstrated herein.

The present invention will be illustrated in detail in the following examples. These examples are included for illustrative purposes and should not be considered to limit the present invention.

EXAMPLE 1

IL-1 Release From Pentamidine Exposed Rat Pulmonary Alveolar Macrophages

Pulmonary alveolar macrophages were collected by lavaging the lungs as previously described (D. B. Warheit et al., Am. Rev. Resp. Dis. 134, 128 (1986)). Once washed and resuspended, the macrophages were allowed to adhere to plastic plates in serum free RPMI 1640 containing 25 mM Hepes, 2 mM L-glutamine, 50 μg/ml gentamicin and streptomycin (media). Following adherence for 1 hour at 37° C. in 5% $CO_2$, the plates were washed once with warm media to remove nonadherent cells, cells were resuspended in media with 10%

FCS and treated with or without pentamidine at the indicated concentration and LPS (5 ng/ml) for 24 hours). IL-1 activity was assayed using a thymocyte co-stimulation assay (S. B. Mizel in Methods in Macrophage Biology, Editors, Herscowitz and Holden (1981)). Single cell thymocyte suspension from B6C3F1 mice (female, 5-9 weeks old) at a concentration of $2.0 \times 10^7$/ml in media containing 10% FCS, and $2.5 \times 10^{-5}$M 2-$\beta$ mercaptoethanol were added in 50 $\mu$l aliquots to each well of flat bottom microtiter plates along with 50 $\mu$l of PHA at 2.5 $\mu$g/ml. Serial dilution of supernatants or cells were made in media with 10% FCS and added in 100 $\mu$l aliquots. IL-1 activity was measured by quantifying the uptake of 3Hthymidine during the last 6 hours of a 72 hour culture at 37° C. and 5% $CO_2$. Cells were harvested onto glass fiber filters and filter associated radioactivity counted in a scintillation counter.

The results are shown in FIG. 1a where it may be seen that IL-1 release from pentamidine exposed rat pulmonary alveolar macrophages decreased in a concentration dependent manner.

EXAMPLE 2

Northern Blot Analysis of IL-1$\alpha$ RNA Expression

For determination of IL-1 mRNA levels, cells ($4 \times 10^6$) were cultured with or without pentamidine (10 $\mu$M) or dexamethasone (1 $\mu$M) in media with 10% FCS in the presence or absence of LPS (1 $\mu$g/ml) for 3 hours. Total cellular RNA was isolated by quanidinium-thiocyanate phenolchloroform extraction (P. Chomczynski et al., Anal. Bioch. 162, 156 (1987)). RNA (10 $\mu$g) was electrophoresed in 1.2% agarose gels as previously described (H. Leharch et al., Biochemistry 4743 (1977)). After electrophoresis, the gels were equilibrated in 10X SSC (1.5 M sodium chloride, 0.15M sodium citrate, pH 7.0) and transferred to Gene Screen Plus membrane (Du Pont) for capillary blot (E. M. Southern, J. Mol. Biol. 98, 503 (1975)). The RNA was fixed by UV-crosslinking for 5 minutes at 300 nm. The blot was hybridized with a 32P radiolabeled mouse IL-1$\alpha$ oligonucleotide probe by an oligonucleotide 3' end labeling system (Du Pont). Hybridization was carried out at 37° C. in 50% formamide, 1M sodium chloride, 10% dextran sulfate and 1% SDS, heated denatured salmon sperm DNA (250 $\mu$g/ml). The filter was washed 2$\times$ at room temperature in 1.0X SSC and 0.1% SDS and 2$\times$ in 0.1 XSSC and 1% SDS. Hybridizing species were detected by autoradiography at $-70$° C., using Kodak XAR film with an intensifying screen. The total RNA levels per lane on the gel was assessed by monitoring 28S and 18S, and expression of $\alpha$-tubulin mRNA. Accumulation of $\alpha$-tubulin mRNA was determined by probing the same blot with $^{32}$P labeled 30 mer oligonucleotide (Du Pont).

The results set forth in FIG. 2 show that both untreated cells (lane A) and pentamidine treated cells (lane B) expressed equal amounts of L-1$\alpha$ mRNA, indicating that blockage of cytokine secretion by pentamidine is not at the level of transcription.

EXAMPLE 3

Western Blot Analysis of Cell Associated IL-1$\alpha$

Cells ($4 \times 10^6$ cells) were oultured with pentamidine (10$\mu$M) or dexamethasone (1$\mu$M) in media with 10% fetal calf serum (FCS) in the presence or absence of LPS (1 $\mu$g/ml) for 24 hours. The cells were washed twice in HBSS and then scraped in homogenizing buffer (HBSS containing 0.1 mM EGTA, 1 mM pmsf, 10 $\mu$g/ml leupeptin, 1 KIU/ml aprotinin, pH 7.4). The cell suspension was left on ice for 10 minutes at which time the swollen cells were disrupted by sonication. The nuclei and undisrupted cells were pelleted by centrifugation at 800 rpm for 10 minutes and were discarded. The supernatant was centrifugated at 39,000 rpm for 1 hour at 4° C. After centrifugation, the supernatants containing cytosolic components of the cell was carefully removed and was used as the cytosol fraction. The pellet was resuspended in homogenizing buffer and used as the particulate fraction. The sample were boiled in Laemmli sample buffer for 5 minutes and then electrophoresed (20 $\mu$g of protein) into a 10-20% SDS polyacrylamide gel with a 4% stacking gel. (U. K. Laemmli, Nature 277, 680 (1970)). After electrophoresis, the gel was equilibrated for 30 minutes in 20 mM tris, 100 mM glycine, 20% methanol, pH 8.8 (tris buffer) and was transferred to a nitrocellulose membrane overnight at 100 mA using tris buffer. After transferring proteins to membrane, IL-1$\alpha$ was visualized by using rabbit antimurine IL-1$\alpha$ as the primary antibody (1:100 diluted) and goat anti-rabbit immunoglobulin conjugated with alkaline phosphatase as the secondary antibody (Immuno-blot assay kit, Bio-Rad). The primary antibody was tested previously for neutralization of rat IL-1$\alpha$ and found to inhibit in a dose related manner bioactive IL-1$\alpha$ as assayed by thymocyte co-stimulation assay. Molecular weight references were determined by running one lane with pre-stained molecular weight standards.

The results shown in the Western blot analysis of FIG. 3 demonstrate that pentamidine allows proper translation of the protein, while dexamethasone does not.

EXAMPLE 4

Effect of Pentamidine on Membrane IL-1

Membrane IL-1 was assayed as previously described (E. A. Kurt-Jones et al, Proc. Natl. Acad. Sci. USA, 82, 1204 (1985)). $10^5$ cells were cultured in media and 10% FCS with or without pentamidine at varying concentrations and LPS at 5 ng/ml for 24 hours and then fixed to the bottom of the 96 well plates with paraformaldehyde. The IL-1 bioassay was then performed as described in Example 1.

The results are shown in FIG. 4, where it may be seen that the amount of bioactive mIL-1 was increased in a dose related manner in pentamidine exposed cells.

EXAMPLE 5

Human Alveolar Macrophage Studies

Four normal healthy human volunteers were lavaged and their pulmonary macrophages cultured in vitro in the presence of $10^{-5}$M pentamidine and the IL-1 inducer, lipopolysaccharide. Following 24 hours of incubation, the supernatant fluid was collected and stored at $-20$° C. for IL-1 determination using an enzyme linked immunosorbant assay with specific antibody to human IL-1. The results are shown in Table 1 below.

TABLE 1

|  | Control* | Pentamidine* |
|---|---|---|
| Individual 1 | 7.7 | 1.3 |
| Individual 2 | 4.6 | 1.0 |
| Individual 3 | 6.2 | 4.3 |

TABLE 1-continued

|  | Control* | Pentamidine* |
|---|---|---|
| Individual 4 | 4.6 | 2.2 |

*values represent mg/ml IL-1 per $10^6$ human cells

IL-1 production by pentamidine treated cells from these four human subjects cumulatively demonstrated a 62.1% suppression in the amount of IL-1 secreted (control values derive from macrophages of the same individual that were not exposed to drug). These data clearly demonstrate that the inhibitory effects of pentamidine on IL-1 are not confined to rodents and cross species barriers effectively.

EXAMPLE 6

Immunomodulation by Pentamidine and Dexamethasone

TABLE 2

|  | Is Antigen[a] Expression (MFI) | Phagocytic Index (%) |
|---|---|---|
| Control | 459 | 32 |
| Pentamidine ($10^{-5}$M) | 464 | 32 |
| Dexamethasone ($10^{-6}$M) | 253* | 25* |

*denotes statistically different from control values (p value < 0.025) as determined by Students T test.

[a]Ia antigen expression - Alveolar macrophages were diluted to $1\times10^6$ cells/ml in RPMI (supplemented as above). Three mls. ($3\times10^6$ cells) were added to sterile teflon vials and treated with pentamidine or dexamethasone for 4 hours at 37° C., 5% $CO_2$, followed by the addition of rat $\gamma$IFN at 100 U/ml. Cells were incubated for 18 hours, pelleted, counted and adjusted to $1\times10^7$ cells/ml in ice cold standard buffer (HBSS, 0.1% Na azide, 1% BSA).

Aliquots of cells (50 μl in quadruplicate) from the various treatment groups were plated to a 96 well round bottom plate (Linbro) and incubated for 45 minutes on ice with 50 μl aliquots of one of the following: monoclonal anti-rat OXS (Sera-lab), monoclonal anti-mouse OX6 (Sera-lab), both at 0.5 μg/$5\times10^5$ cells, or HBSS (control). Cells were washed 3× with standard buffer and incubated for 45 minutes on ice, in the dark, with 50 μl of phycoerythrin-labeled goat anti-mouse IGGI (Fisher Biotech) at 1 μg/$5\times10^5$ cells. Cells were washed 3× with standard buffer, resuspended in 0.4 ml of standard buffer and analyzed via flow cytometry.

[b]Phagocytosis - Pulmonary alveolar macrophages were adjusted to $1\times10^6$ cells/ml in RPMI 1640 containing 10% FCS (supplemented as above). One ml aliquots were added to sterile teflon vials (Nalgene) along with pentamidine or dexamethasone (Sigma) as indicated, and incubated for 4 hours at 37° C., 5% $CO_2$. Fluoresbrite carboxylate beads, 1.73 μm (Polysciences) were used to achieve a 100:1 bead to cell ratio and the suspension was incubated for 45 minutes at 37° C., 5% $CO_2$ with gentle agitation. Cell suspensions were then layered over 3 mls. of RPMI/FCS+0.3% BSA, and cells pelleted at 150 xg for 10 minutes. Supernates were discarded and cells resuspended in 1 ml of RPMI/FCS for analysis via flow cytometry. The data presented above is the mean of the percentage of cells taking up one or more beads of triplicate cultures.

EXAMPLE 7

Endotoxemia Following Pentamidine Administration

Hypothermia and Survival

Female B6C3F1 mice weighing approximately 24 g were dosed with pentamidine (15 mg/kg.; i.v.) at both 24 hours and 1 hour prior to LPS administration (50 mg/kg; i.p.). Temperature response indices (TRI) were determined for the period between time zero and +12 hours in groups of 5 mice. Table 3 below also shows the mean rectal temperatures at time zero ($Tr_0$) and 12 hours ($Tr_{12}$). Animals used for body temperature measurements were treated identically and on the same day as those animals for which survival was measured, although the survival of these animals is not included in the Table below. Survival data shown in Table 3 is following 24 hours of observation.

TABLE 3

| | Body Temp °C. (°C. ± SE) | | | |
|---|---|---|---|---|
| | TRI (Δ°C. ± SE) | $Tr_0$ (°C. ± SE) | $Tr_{12hr}$ (°C. ± SE) | Survival |
| VEHICLE | −1.3 | 38.2 ± 0.1 | 36.9 ± 1.4 | 10/10 |
| PENTAMIDINE | −2.4 | 37.4 ± 0.6 | 35.0 ± 2.9 | 9/9 |
| LPS | −13.3 | 38.6 ± 0.4 | 25.3 ± 0.5 | 0/10 |
| PENTAMIDINE + LPS | −8.3* | 37.3 ± 0.4 | 29.0 ± 2.2* | 10/10* |

*Denotes statistically different from LPS group alone (P < 0.01).

EXAMPLE 8

Effect of Pentamidine Isethionate on the Ear Swelling Response to Oxazolone

All groups were sensitized with 25 μl of 2.0% oxazolone on day 0 on the shaved dorsal surface of the back. On day 5, each group was treated with 10 μl of pentamidine on each side of the right ear immediately prior to challenge with 10 μl of 0.5% oxazolone on each side of the right ear. The left ear was treated at same time with the oxazolone vehicle (4:1 acetone:olive oil) and in the same manner as the challenged ear. Ear thickness was determined before, 24 and 48 hours after challenge. The concentration of pentamidine for each group was as follows:

Group 1—80 μg/ear pentamidine
Group 2—40 μg/ear pentamidine
Group 3—20 μg/ear pentamidine
Group 4—10 μg/ear pentamidine
Group 5—5 μg/ear pentamidine
Group 6—no treatment (oxazolone positive control)

The results shown in FIG. 5 indicate that treating mice with pentamidine eipcutaneously at the time of challenge resulted in a statistically significant (p<0.001) reduction in the hypersensitivity response as measured by ear swelling. It is concluded that dermal application of pentamidine at the time of challenge with oxazolone is sufficient to produce a statistically significant reduction in ear swelling as a measure of delayed-type hypersensitivity.

EXAMPLE 9

Alveolar Macrophage Viability Following Exposure to Pentamidine

Alveolar macrophage viability was assessed by incubating the cells in RPMI 1640 media with 10% fetal calf serum in the presence of pentamidine at the indicated concentrations. Twenty-four hours later the cells were analyzed for viability using ethidium bromide staining. A minimum of 10,000 cells were analyzed by flow cytometry on a FACSCAN analyzer.

The results are shown in FIG. 6. These observations have been confirmed using microscopic analysis via trypan blue dye exclusion.

Figure 6A:
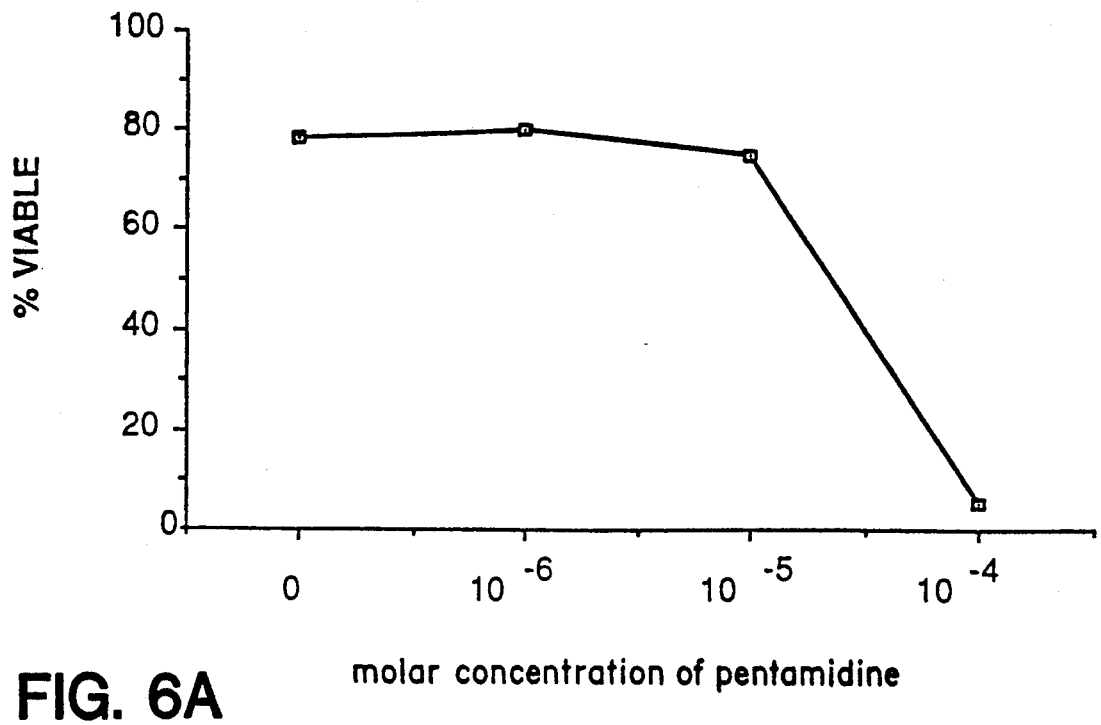

FIG. 6(a) shows the pulmonary alveolar macrophage viability following 24 hour exposure to pentamidine at a molar concentration in the range of 0 to $10^{-4}$M.

Figure 6B:
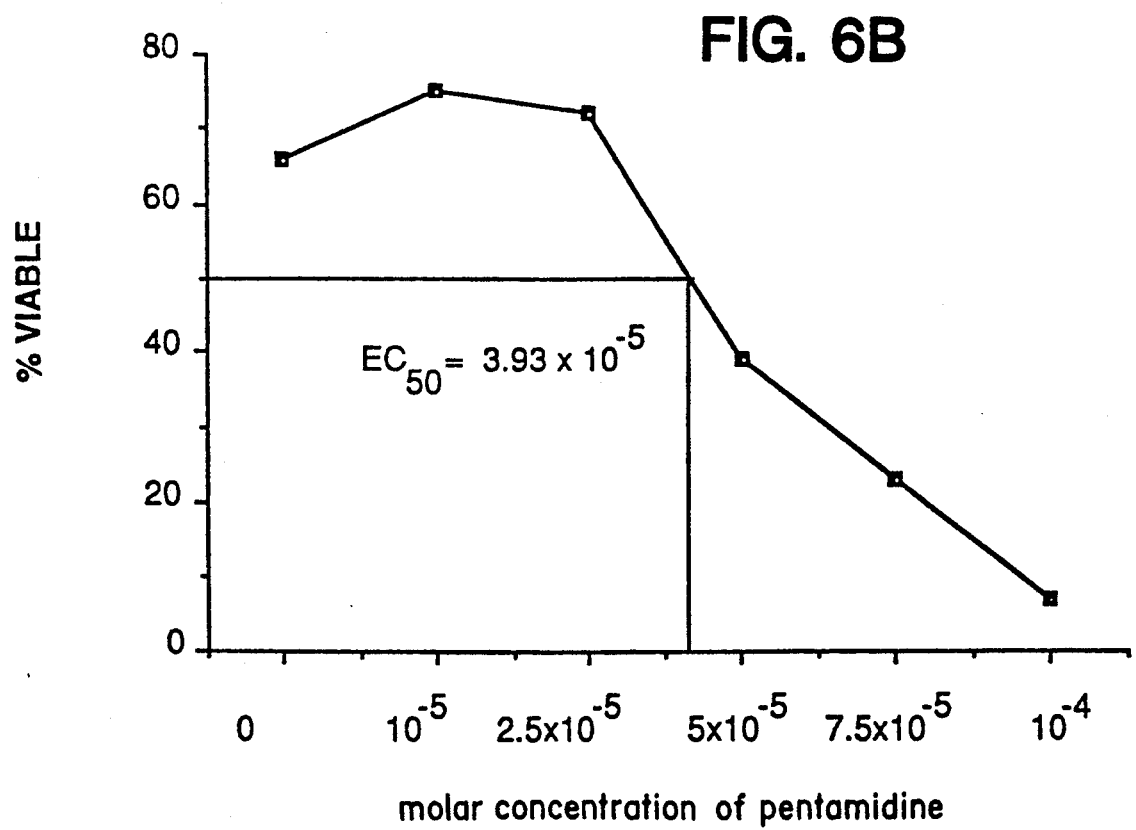

FIG. 6(b) is an expanded view of the FIG. 6(a) graph showing the pulmonary alveolar macrophage viability following 24 hour exposure to pentamidine at a molar concentration in the range of $10^{-4}$M to $10^{-5}$M.

EXAMPLE 10

Effect of an Imidazoline on Secretion of IL-1 and Tumor Necrosis Factor

In vitro studies were performed by taking alveolar macrophages from normal healthy rat lungs and culturing them in the presence of an imidazoline with the inducer lipopolysaccharide for 24 hours. The standard bioassay for IL-1 was performed (see above). As shown in FIG. 7, the imidazoline blocked IL-1 in a dose related manner at $10^{-6}$M, $10^{-5}$M and $10^{-4}$M. No effect was observed at $10^{-8}$M. Similar observations were observed with bioassays for tumor necrosis factor.

TABLE 4

| Tumor Necrosis Factor (units/ml at $10^{-5}$M Imidazoline) ||
| Control | Imidazoline |
| --- | --- |
| 83 ± 11 | 46 ± 19 |

In addition, Western blot analysis of IL-1 on cellular protein derived from imidazoline treated cells was recently performed. This method definitively identifies the presence or absence of the protein using electrophoretic techniques to separate by molecular weight IL-1 from other proteins followed by staining with specific antibody fog IL-1. This very sensitive technique confirmed the bioassay determination that this compound blocks the secretion of IL-1 in a similar manner to pentamidine.

The invention having been described, it will be appreciated by those skilled in the art, that various modifications in form and detail can be made without departing from the true scope of the invention.

What is claimed is:

1. A method for inhibiting the release of interleukin 1 from interleukin 1 producing cells, comprising contacting said cells with an amount of an aromatic diamidine sufficient to inhibit interleukin 1 release from said cells, wherein said cells are in a human afflicted with an inflammatory disease or condition selected from the group consisting of arthritis, skin hypersensitivity, glomerulonephritis, septicemia, endotoxemia, pulmonary granulomas, pulmonary fibrosis, cirrhosis, sarcoidosis, tuberculosis, chronic granulomatous disease, dysfunctional clot formation and transplant rejection, and diseases and conditions associated with the release of acute phase reactants by hepatocytes.

2. The method of claim 1, wherein the aromatic diamidine is administered to the human in the form of an aerosol.

3. The method of claim 2, wherein the aromatic diamidine is administered to the human in the form of an aerosol at a dosage of up to 650 mg per dose of active ingredient.

4. The method of claim 3, wherein the aromatic diamidine is administered to the human at a dosage of about 300 mg per dose.

5. The method of claim 1, wherein the aromatic diamidine is injected in the human.

6. The method of claim 5, wherein the aromatic diamidine is injected in the human at a dosage of up to 15 mg active ingredient/kg human.

7. The method of claim 5, wherein the aromatic diamidine is injected in the human subcutaneously.

8. The method of claim 5, wherein the aromatic diamidine is injected in the human intrasmuscularly.

9. The method of claim 1, wherein the aromatic diamidine is administered in the human dermally.

10. The method of claim 9, wherein the aromatic diamidine is administered to the human dermally at a concentration of up to 1% active ingredient in solution.

11. The method of claim 1, wherein the inflammatory disease is arthritis.

12. The method of claim 1, wherein the inflammatory disease is a hypersensitivity disease.

13. The method of claim 1, wherein the inflammatory disease is endotoxemia.

14. A method for inhibiting release of interleukin 1 from interleukin 1 producing cells, comprising contacting said cells with an amount of an aromatic diamidine sufficient to inhibit the interleukin 1 release from said cells.

15. The method of claim 14, wherein the aromatic diamidine is 1,5-bis(4-amidinophenoxy)pentane.

16. The method of claim 15, wherein the 1,5-bis(4-amidinophenoxy)pentane is in the form of pentamidine isethionate.

17. The method of claim 14, wherein the aromatic diamidine is an imidazoline.

18. The method of claim 17, wherein the imidazoline is in the form of 1,5-di(4-imidazolinophenoxy)pentane.

19. A method for inhibiting release of tumor necrosis factor from tumor necrosis factor producing cells, comprising contacting said cells with an amount of an aromatic diamidine sufficient to inhibit the tumor necrosis factor release from said cells.

20. The method of claim 19, wherein the aromatic diamidine is 1,5-bis(4-amidinophenoxy)pentane.

21. The method of claim 20, wherein the 1,5-bis(4-amidinophenoxy)pentane is in the form of pentamidine isethionate.

22. The method of claim 19, wherein the aromatic diamidine is an imidazoline.

23. The method of claim 22, wherein the imidazoline is in the form of 1,5-di(4-imidazolinophenoxy)pentane.

24. A method for inhibiting release of interleukin 6 from interleukin 6 producing cells, comprising contacting said cells with an amount of an aromatic diamidine sufficient to inhibit the interleukin 6 release from said cells.

25. The method of claim 24, wherein the aromatic diamidine is 1,5-bis(4-amidinophenoxy)pentane.

26. The method of claim 25, wherein the 1,5-bis(4-amidinophenoxy)pentane is in the form of pentamidine isethionate.

27. The method of claim 24, wherein the aromatic diamidine is an imidazoline.

28. The method of claim 27, wherein the imidazoline is in the form of 1,5-di(4-imidazolinophenoxy)pentane.

* * * * *